United States Patent
Pirot

(10) Patent No.: US 9,249,452 B2
(45) Date of Patent: Feb. 2, 2016

(54) METHOD OF DETECTING AND ASSAYING TELOMERASE ACTIVITY OF TELOMERASE BOUND BY ANTI-TELOMERASE ANTIBODIES

(76) Inventor: Zhu Zhen Pirot, Redwood City, CA (US)

( * ) Notice: Subject to any disclaimer, the term of this patent is extended or adjusted under 35 U.S.C. 154(b) by 0 days.

(21) Appl. No.: 13/035,469

(22) Filed: Feb. 25, 2011

(65) Prior Publication Data
US 2011/0212454 A1  Sep. 1, 2011

Related U.S. Application Data

(60) Provisional application No. 61/308,636, filed on Feb. 26, 2010.

(51) Int. Cl.
*C12Q 1/68* (2006.01)
*C12Q 1/48* (2006.01)

(52) U.S. Cl.
CPC ........ *C12Q 1/48* (2013.01); *G01N 2333/91245* (2013.01)

(58) Field of Classification Search
USPC ............ 435/6, 91.2, 183, 184, 15, 1.52, 91.5, 435/366, 6.19, 7.5, 6.12, 174; 536/24.33, 536/23.1, 24.31; 424/94.1; 436/63, 64
See application file for complete search history.

(56) References Cited

U.S. PATENT DOCUMENTS

| | | | |
|---|---|---|---|
| 5,629,154 A * | 5/1997 | Kim et al. ......................... | 435/6 |
| 5,639,613 A | 6/1997 | Shay et al. | |
| 5,648,215 A * | 7/1997 | West et al. ......................... | 435/6 |
| 5,693,474 A | 12/1997 | Shay et al. | |
| 5,695,932 A | 12/1997 | West et al. | |
| 5,804,380 A | 9/1998 | Harley et al. | |
| 5,837,453 A | 11/1998 | Harley et al. | |
| 5,863,726 A * | 1/1999 | Harley et al. ...................... | 435/6 |
| 5,891,639 A * | 4/1999 | Harley et al. ................... | 435/6.12 |
| 6,221,584 B1 | 4/2001 | Emrich et al. | |
| 6,391,554 B1 | 5/2002 | West et al. | |
| 7,285,639 B2 | 10/2007 | Cech et al. | |
| 7,750,121 B2 | 7/2010 | Cech et al. | |
| 2003/0190638 A1* | 10/2003 | West et al. ......................... | 435/6 |
| 2009/0142770 A1* | 6/2009 | Go et al. ........................... | 435/6 |
| 2009/0208932 A1 | 8/2009 | Nice et al. | |

FOREIGN PATENT DOCUMENTS

| | | | | |
|---|---|---|---|---|
| WO | WO-97/20069 | | 6/1997 | |
| WO | WO9814593 | * | 4/1998 | ............. C12N 15/54 |
| WO | WO0046601 | * | 8/2000 | ............ G01N 33/573 |
| WO | WO2008002285 | * | 1/2008 | ............. C07K 16/40 |

OTHER PUBLICATIONS

Cohen SB, Reddel RR. A sensitive direct human telomerase activity assay. Nature Methods. 2008. 5(4):355-60.*
Norton JC, Piatyszek MA, Wright WE, Shay JW, Corey DR. Inhibition of human telomerase activity by peptide nucleic acids. Nat Biotechnol. 1996. 14(5):615-9.*
Huang YP, Liu ZS, Tang H, Liu M, Li X. Real-time telomeric repeat amplification protocol using the duplex scorpion and two reverse primers system: the high sensitive and accurate method for quantification of telomerase activity. Clin Chim Acta. 2006. 372(1-2):112-9. Epub Mar. 29, 2006.*
Supplementary_Cohen_2008_NatureMethods_Direct-TelomeraseAssay.pdf.*
Sun D. Biotinylated primer for detecting telomerase activity without amplification. Methods Mol Biol. 2002. 191:165-71. Review.*
Fajkus J. Detection of telomerase activity by the TRAP assay and its variants and alternatives. Clin Chim Acta. 2006.371(1-2):25-31. Epub Apr. 17, 2006. Review.*
Zhou X, Xing D, Zhu D, Jia L. Magnetic bead and nanoparticle based electrochemiluminescence amplification assay for direct and sensitive measuring of telomerase activity. Anal Chem. 2009. 81(1):255-61.*
Wege H, Chui MS, Le HT, Tran JM, Zern MA. SYBR Green real-time telomeric repeat amplification protocol for the rapid quantification of telomerase activity. Nucleic Acids Res. 2003. 31(2):E3-3.*
Liu X, Dakic A, Zhang Y, Dai Y, Chen R, Schlegel R. HPV E6 protein interacts physically and functionally with the cellular telomerase complex. Proc Natl Acad Sci U S A. Nov. 3, 2009;106(44):18780-5.*
Klapper W, Moosig F, Sotnikova A, Qian W, Schröder JO, Parwaresch R. Telomerase activity in B and T lymphocytes of patients with systemic lupus erythematosus. Ann Rheum Dis. 2004. 63(12):1681-3.*
Xiao Y, Gao X, Gannot G, Emmert-Buck MR, Srivastava S, Wagner PD, Amos MD, Barker PE. Quantitation of HER2 and telomerase biomarkers in solid tumors with IgY antibodies and nanocrystal detection. Int J Cancer. May 15, 2008; 122(10):2178-86.*
Xiang H, Wang J, Mao YW, Li DW. hTERT can function with rabbit telomerase RNA:regulation of gene expression and attenuation of apoptosis. Biochem Biophys Res Commun. 2000.30; 278(3):503-10.*
Kraveka JM, Schady D, Obeid LM, Ogretmen B. Immunoprecipitation of human telomerase reverse transcriptase with telomerase activity. Anal Biochem. Apr. 1, 2001;291(1):166-9.*
Soldateschi D, Bravaccini S, Berti B, Brogi A, Benicchi T, Soldatini C, Medri L, Fabbri F, De Paola F, Amadori D, Calistri D. Development and characterization of a monoclonal antibody directed against human telomerase reverse transcriptase (hTERT). J Biotechnol. Sep. 10, 2005;118(4):370-8.*
Cohen SB, Reddel RR. A sensitive direct human telomerase activity assay. Nat Methods. 2008. 5(4):355-60.*

(Continued)

*Primary Examiner* — Samuel Woolwine
*Assistant Examiner* — Olayinka Oyeyemi
(74) *Attorney, Agent, or Firm* — Leslie A. Mooi

(57) ABSTRACT

The invention is directed to methods for determining the level of telomerase reverse transcriptase activity in mammalian cells. The method comprises binding the telomerase reverse transcriptase obtained from the mammalian cells to a solid support by contacting the telomerase with an anti-telomerase antibody bound to a solid support and then measuring the level of activity of the bound telomerase in a reaction where the telomerase can extend a first primer to produce an extension product and qualitatively or quantitatively detecting the extension product.

22 Claims, 8 Drawing Sheets

(56) References Cited

OTHER PUBLICATIONS

Cohen, S. et al., "A sensitive direct human telomerase activity assay", *Nature Methods* 5(4), (2008), pp. 355-360.

Cohen, S. et al., "Protein composition of catalytically active human telomerase from immortal cells", *Science* 315, (2007), pp. 850-853.

Cohen, S. et al., "Supporting Online Material for Protein Composition of Catalyticaly Active Human Teloomerase from Immortal Cells", *Science 315*, Suppl. (Materials and Methods, Figs. S1-S5, Table S1, and References), (2007), 25 pages.

PCT Search Report for PCT/US2011/026281, dated Apr. 12, 2011 3 pages.

* cited by examiner

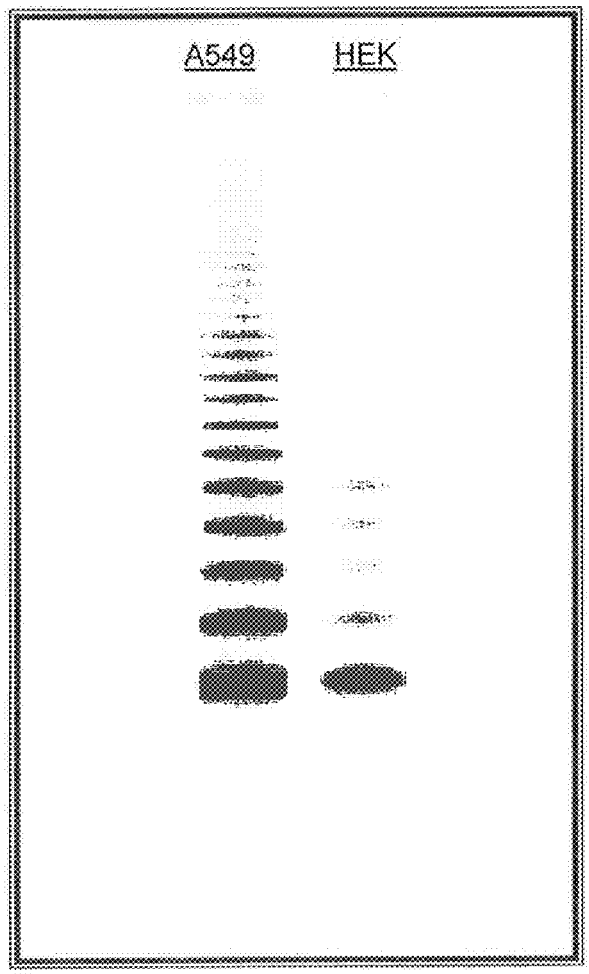
Figure 2: Cell line extract with IP TRAP

Fig. 5 Human telomerase reverse transcriptase

```
Met Pro Arg Ala Pro Arg Cys Arg Ala Val Arg Ser Leu Leu Arg Ser
 1           5                   10                  15
His Tyr Arg Glu Val Leu Pro Leu Ala Thr Phe Val Arg Arg Leu Gly
            20                  25                  30
Pro Gln Gly Trp Arg Leu Val Gln Arg Gly Asp Pro Ala Ala Phe Arg
        35                  40                  45
Ala Leu Val Ala Gln Cys Leu Val Cys Val Pro Trp Asp Ala Arg Pro
    50                  55                  60
Pro Pro Ala Ala Pro Ser Phe Arg Gln Val Ser Cys Leu Lys Glu Leu
65                  70                  75                  80
Val Ala Arg Val Leu Gln Arg Leu Cys Glu Arg Gly Ala Lys Asn Val
                85                  90                  95
Leu Ala Phe Gly Phe Ala Leu Leu Asp Gly Ala Arg Gly Gly Pro Pro
            100                 105                 110
Glu Ala Phe Thr Thr Ser Val Arg Ser Tyr Leu Pro Asn Thr Val Thr
            115                 120                 125
Asp Ala Leu Arg Gly Ser Gly Ala Trp Gly Leu Leu Leu Arg Arg Val
    130                 135                 140
Gly Asp Asp Val Leu Val His Leu Leu Ala Arg Cys Ala Leu Phe Val
145                 150                 155                 160
Leu Val Ala Pro Ser Cys Ala Tyr Gln Val Cys Gly Pro Pro Leu Tyr
                165                 170                 175
Gln Leu Gly Ala Ala Thr Gln Ala Arg Pro Pro Pro His Ala Ser Gly
            180                 185                 190
Pro Arg Arg Arg Leu Gly Cys Glu Arg Ala Trp Asn His Ser Val Arg
        195                 200                 205
Glu Ala Gly Val Pro Leu Gly Leu Pro Ala Pro Gly Ala Arg Arg Arg
    210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
                245                 250                 255
Ala His Pro Gly Arg Thr Arg Gly Pro Ser Asp Arg Gly Phe Cys Val
            260                 265                 270
Val Ser Pro Ala Arg Pro Ala Glu Glu Ala Thr Ser Leu Glu Gly Ala
        275                 280                 285
Leu Ser Gly Thr Arg His Ser His Pro Ser Val Gly Arg Gln His His
    290                 295                 300
Ala Gly Pro Pro Ser Thr Ser Arg Pro Pro Arg Pro Trp Asp Thr Pro
305                 310                 315                 320
Cys Pro Pro Val Tyr Ala Glu Thr Lys His Phe Leu Tyr Ser Ser Gly
                325                 330                 335
Asp Lys Glu Gln Leu Arg Pro Ser Phe Leu Leu Ser Ser Leu Arg Pro
            340                 345                 350
Ser Leu Thr Gly Ala Arg Arg Leu Val Glu Thr Ile Phe Leu Gly Ser
        355                 360                 365
Arg Pro Trp Met Pro Gly Thr Pro Arg Arg Leu Pro Arg Leu Pro Gln
    370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
            420                 425                 430
Gly Ser Val Ala Ala Pro Glu Glu Glu Asp Thr Asp Pro Arg Arg Leu
        435                 440                 445
Val Gln Leu Leu Arg Gln His Ser Ser Pro Trp Gln Val Tyr Gly Phe
    450                 455                 460
```

Fig. 5 continued

```
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
            485                 490                 495
Leu Gly Lys His Ala Lys Leu Ser Leu Gln Glu Leu Thr Trp Lys Met
                500                 505                 510
Ser Val Arg Asp Cys Ala Trp Leu Arg Arg Ser Pro Gly Val Gly Cys
        515                 520                 525
Val Pro Ala Ala Glu His Arg Leu Arg Glu Glu Ile Leu Ala Lys Phe
    530                 535                 540
Leu His Trp Leu Met Ser Val Tyr Val Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
        595                 600                 605
His Arg Glu Ala Arg Pro Ala Leu Leu Thr Ser Arg Leu Arg Phe Ile
    610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro Pro
    690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
        755                 760                 765
Leu Gln Pro Tyr Met Arg Gln Phe Val Ala His Leu Gln Glu Thr Ser
    770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
        835                 840                 845
Met Glu Asn Lys Leu Phe Ala Gly Ile Arg Arg Asp Gly Leu Leu Leu
    850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
Val Val Asn Leu Arg Lys Thr Val Val Asn Phe Pro Val Glu Asp Glu
            900                 905                 910
Ala Leu Gly Gly Thr Ala Phe Val Gln Met Pro Ala His Gly Leu Phe
        915                 920                 925
```

Fig. 5 Continued

Pro Trp Cys Gly Leu Leu Leu Asp Thr Arg Thr Leu Glu Val Gln Ser
            930                 935                 940
Asp Tyr Ser Ser Tyr Ala Arg Thr Ser Ile Arg Ala Ser Leu Thr Phe
945                 950                 955                 960
Asn Arg Gly Phe Lys Ala Gly Arg Asn Met Arg Arg Lys Leu Phe Gly
                965                 970                 975
Val Leu Arg Leu Lys Cys His Ser Leu Phe Leu Asp Leu Gln Val Asn
            980                 985                 990
Ser Leu Gln Thr Val Cys Thr Asn Ile Tyr Lys Ile Leu Leu Leu Gln
        995                 1000                1005
Ala Tyr Arg Phe His Ala Cys Val Leu Gln Leu Pro Phe His Gln Gln
        1010                1015                1020
Val Trp Lys Asn Pro Thr Phe Phe Leu Arg Val Ile Ser Asp Thr Ala
1025                1030                1035                1040
Ser Leu Cys Tyr Ser Ile Leu Lys Ala Lys Asn Ala Gly Met Ser Leu
                1045                1050                1055
Gly Ala Lys Gly Ala Ala Gly Pro Leu Pro Ser Glu Ala Val Gln Trp
            1060                1065                1070
Leu Cys His Gln Ala Phe Leu Leu Lys Leu Thr Arg His Arg Val Thr
        1075                1080                1085
Tyr Val Pro Leu Leu Gly Ser Leu Arg Thr Ala Gln Thr Gln Leu Ser
        1090                1095                1100
Arg Lys Leu Pro Gly Thr Thr Leu Thr Ala Leu Glu Ala Ala Ala Asn
1105                1110                1115                1120
Pro Ala Leu Pro Ser Asp Phe Lys Thr Ile Leu Asp
                1125                1130

METHOD OF DETECTING AND ASSAYING TELOMERASE ACTIVITY OF TELOMERASE BOUND BY ANTI-TELOMERASE ANTIBODIES

This application is a claims priority to US provisional Application No. 61/308,636, filed Feb. 26, 2010, which is incorporated by reference in its entirety.

FIELD OF THE INVENTION

The invention is directed to a method for the detection or measurement of telomerase activity as well as reagents suitable therefore.

BACKGROUND

Telomeres are genetic elements located at the ends of all eukaryotic chromosomes which preserve genome stability and cell viability by preventing aberrant recombination and degradation of DNA. In humans, the telomeric sequence is composed of 10-20 kilobases of TTAGGG repeats (Blackburn, (1991) Nature vol. 350 pp 569-573). There is increasing evidence that gradual loss of telomeric repeat sequences may be a timing ("clock") mechanism limiting the number of cellular divisions in normal somatic cells (Harley et al., (1990) Nature, vol. 345, pp. 458-460). In contrast, immortal cells are capable of maintaining a stable telomere length by upregulating or reactivating telomerase, a ribonucleoprotein enzyme that is able to add TTAGGG repeats to the ends of chromosomes (Greider and Blackburn, (1989) Nature, vol. 337, pp. 331-337; Morin, (1989) Cell, vol. 59, pp. 521-529).

Telomerase activity has been detected in 85% of primary human tumors tested from a variety of tissue types (Kim et al., (1994) Science, vol. 266, pp. 2011-2015; Shay and Bacchetti, (1997) European Journal of Cancer, vol. 33, No. 5, pp. 787-791). The detection of high telomerase activity in human cells or tissues almost always correlates with indefinite proliferation capability (immortalization). U.S. Pat. No. 5,648,215 describes the presence of telomerase activity in somatic cells as indicative of the presence of immortal cells, such as certain types of cancer cells, which can be used to make that determination even when the cells would be classified as non-cancerous by pathology. In addition, when telomerase assays are performed on certain normal stem cell compartments (e.g. bone marrow) or in regions of highly proliferative cells (e.g. hair follicles and crypt gut epithelial cells), and a high level of telomerase activity is detected, this can be indicative of active regenerating tissue.

Methods for detecting telomerase activity, as well as for identifying compounds that regulate or affect telomerase activity, have been described. See PCT patent publication No. 93/23572, U.S. Pat. Nos. 5,629,154, 5,648,215, 5,645,986, 5,695,932 and 5,489,508. Each of the foregoing patent publications is incorporated herein by reference.

For example, U.S. Pat. Nos. 5,629,154; 5,863,726 and 5,648,215 describe in detail the preparation of a cell extract using a detergent lysis method and the analysis of telomerase activity by the Telomeric Repeat Amplification Protocol (TRAP assay). The telomerase activity assays described therein involve the extension of a synthetic nucleic acid substrate derived from the telomere sequence which serves as a primer. This primer is added together with unlabelled dideoxynucleotides to a sample, e.g. a cell extract suspected of containing telomerase whereby the primer is specifically elongated by the telomerase.

The extended primer may be detected directly by a number of methods. The primer may be directly attached to an anchor group which can be immobilized on a solid phase using any known method. Examples of suitable anchor groups are biotin which can bind with high affinity binding to an immobilized partner such as avidin or streptavidin. Detection of the immobilized primer can be measured by either incorporation of a radioactive deoxynucleotide or by the binding of a sequence specific labeled probe to the extended primer.

The extended substrate may also be detected after it is replicated in a primer extension reaction, such as the polymerase chain reaction (PCR) a radioactive deoxyribonucleoside triphosphate (dNTP) for labeling any telomerase-extended substrate. The reaction mixture is subsequently separated by gel electrophoresis and the pattern of bands visualized. Because telomerase stalls and can release the DNA after adding the first G in the 5'-TTAGGG-3' telomeric repeat, the characteristic pattern of products on the gel is a six nucleotide ladder of extended oligonucleotide substrates. The phase of the repeats depends on the 3'-end sequence of the substrate; telomerase recognizes where the end is in the repeat and synthesizes accordingly to yield contiguous repeat sequences.

However, these detection methods of the state of the art have some disadvantages. The level of telomerase enzyme in human cells containing the enzyme is very low in the order of 10-100 molecules per cell. Therefore, the sensitivity of a direct detection method without an amplification step may be too low for routine applications since quantities of extracts containing >$10^7$ cells typically have to be used for direct detection. Therefore this method cannot be used to examine primary tumor material which is only available in a small amount.

In addition, the gel images of the telomerase products are poor; often appearing as a smear rather than distinct bands, and quantitation of these bands is difficult, imprecise, and inaccurate.

A number of factors contribute to these issues, but the most important factor is likely the impurity of the telomerase extract itself Telomerase is present at roughly 10 ppb (w/w protein) i.e. 0.000001%, in a crude cell extract from telomerase positive cells. In a tissue which contains a mixture of telomerase positive and negative cells, the relative abundance is even lower. The 100 million-fold excess of other proteins that are released upon disruption of the cells into the reaction mixture can interfere with the telomerase activity assay by non binding to the primers, by interference with the activity of the telomerase or the taq (PCR) polymerase enzyme, by degradation of the telomerase or taq enzyme, primers, or probes, or by consumption or binding to other components in the reaction mixture (e.g. dNTPs and metal ions).

Accordingly, neither method is suitable for cells with very low levels of telomerase enzyme or for very small tissue samples. Moreover, neither method allows a high sample throughput. The methods are not suitable for automation as is necessary for example for routine analysis of tissue samples for analysis of telomerase modulators. Identification of a method of isolating the telomerase enzyme and routine analysis for telomerase activity would be beneficial.

SUMMARY OF THE INVENTION

The invention provides a method for measuring telomerase activity comprising isolating the telomerase enzyme on a solid support with an anti-telomerase antibody and measuring the level of activity of the telomerase bound to the solid support.

The invention provides a method for detecting a presence or an amount of telomerase activity, comprising: (a) combining in a reaction vessel (1) an active mammalian telomerase ribonucleoprotein enzyme complex bound to a solid support by an anti-telomerase antibody, (2) a first primer, which is suitable as a telomerase substrate, and (3) a plurality of nucleoside triphosphates to form a reaction mixture, and incubating the reaction mixture under conditions to extend the first primer in an extension reaction to produce an extension product; and (b) qualitatively or quantitatively detecting the extension product and correlating the detection with the presence or amount of telomerase activity.

Another embodiment is a method for detecting a presence or an amount of telomerase activity, comprising: (a) binding an active mammalian telomerase ribonucleoprotein enzyme complex to a solid support with an anti-telomerase antibody, (b) combining in a reaction vessel (1) telomerase ribonucleoprotein enzyme complex bound to the solid support, (2) a first primer, which is suitable as a telomerase substrate, and (3) a plurality of nucleoside triphosphates to form a reaction mixture, and incubating the reaction mixture under conditions to extend the first primer in an extension reaction to produce an extension product; and (c) qualitatively or quantitatively detecting the extension product and correlating the detection with the presence or amount of telomerase activity.

Another embodiment is a method for evaluating the response of a mammalian biological system (e.g. cell, tissue, or mammal) exposed to a telomerase modulator comprising: (a) combining in a reaction vessel (1) an active mammalian telomerase ribonucleoprotein enzyme complex from the system bound to a solid support by an anti-telomerase antibody, (2) a first primer, which is, suitable as a telomerase substrate, and (3) a plurality of nucleoside triphosphates to form a reaction mixture, and incubating the reaction mixture under conditions to extend the first primer in an extension reaction to produce an extension product; and (b) qualitatively or quantitatively detecting the extension product and correlating the amount of extension product with the amount of telomerase activity; (c) comparing the level of telomerase activity after administration of the modulator to a standard telomerase activity to determine the response of the system.

The method wherein the anti-telomerase antibody recognizes and binds human or rat telomerase reverse transcriptase enzyme (hTERT). The method wherein the anti-telomerase antibody recognizes and binds human telomerase. It has been found that the antibody generated to ARPAEEATSLEGALSGTRH (SEQ ID NO:2) (human telomerase (HTERT) amino acids 276 to 293) also recognizes rat telomerase reverse transcriptase.

The method wherein the anti-telomerase antibody is a polyclonal mixture of antibodies comprising antibodies specific for human telomerase enzyme (SEQ ID NO:1). The method wherein the antibody is specific for a 10-19 amino acid peptide sequence from the sequence ARPAEEATSLEGALSGTRH (SEQ ID NO:2) (human telomerase (HTERT) amino acids 276 to 294).

It is contemplated that the primers may be labeled. The label may be selected from the group consisting of a radioactive molecule, a fluorescent molecule, a phosphorescent molecule, a ligand for a receptor, biotin, and avidin.

The method wherein the extension products are immobilized on a solid phase via an anchor group. The anchor group may be biotin and the solid phase may be coated with avidin and/or streptavidin.

It is contemplated that the method may include a further step wherein the extension products are amplified to produce amplification products and qualitatively or quantitatively detecting the amplification products to qualitatively or quantitatively detect the extension product.

In other embodiments, the amplification step of the method comprises adding to said reaction mixture a second primer comprising a sequence sufficiently complementary to a telomeric repeat to hybridize specifically thereto under conditions such that if a telomeric extension product is present in said reaction mixture, said second primer will hybridize to said telomeric extension product and extend to form a complementary copy of said telomeric extension product, thereby forming telomerase repeat amplification products.

The amplification step of the invention may further comprise heating said reaction mixture to denature said telomerase repeat amplification products; and cooling said reaction mixture to a temperature at which complementary nucleic acids can hybridize and said first primer and second primer can extend if extended telomerase substrates are present.

The amplification step may have template-dependent DNA polymerase present in the reaction mixture and said primer may extended by addition of nucleotides to said second primer by said DNA polymerase. The template-dependent DNA polymerase is a thermostable template-dependent DNA polymerase.

In some embodiments, the first primer which is suitable as a telomerase substrate may be labeled. In some embodiments the second primer suitable for amplification may be labeled. Where there is a label, it may be selected from the group consisting of a radioactive molecule, a fluorescent molecule, a phosphorescent molecule, a ligand for a receptor, biotin, and avidin.

In some embodiments the telomerase repeat amplification products are duplex DNA which may be labeled with an intercalating label selected from the group consisting of a radioactive molecule or a fluorescent molecule.

In some embodiments the telomerase substrate lacking a telomeric repeat sequence is 5'-AATCCGTCGAGCAGAGTT-3' (SEQ ID NO:3). In some embodiments, the primer comprises a non-telomeric repeat sequence at a 5'-end of said primer. In some embodiments the primer is 5'-CCCTTACCCTTACCCTTACCCTAA-3' (SEQ ID NO: 4), 5'-GCGCGGCTAACCCTAACCCTAACC-3' (SEQ ID NO:5) or 5'-GCGCGGCTTACCCTTACCCTTACCCTAACC-3' (SEQ ID NO:6).

The amplification products may be immobilized on a solid phase via an anchor group. The anchor group may be biotin and the solid phase may be coated with avidin and/or streptavidin.

It is contemplated that the level of telomerase activity in the biological system will be compared to the level of telomerase activity in the biological system prior to treatment with the telomerase modulator. Alternatively the level of activity might be compared to a standard level of telomerase activity for the type of biological system. A biological response would be an increase or decrease in the level of telomerase activity relative to a standard telomerase for the biological system.

In some embodiments, the method of measuring the telomerase activity further comprises normalizing the level of telomerase activity in the cell extract relative to the amount of RNA or protein in the cell extract. In some embodiments the amount of protein is the total amount of protein in the cell extract. In some embodiments, the amount of RNA in the cell extract is the amount of ribosomal RNA. The amount of ribosomal RNA may be determined by a PCR reaction using primers for the 18S ribosomal RNA. In other embodiments, the amount of RNA in the cell extract may be the amount of mRNA of genes which are specifically expressed in follicle cells.

The mammalian biological system may be cells, tissue or mammals which express telomerase reverse transcriptase. The cells may be cancer cells, skin cells, hair follicle cells, or blood cells. In one embodiment the biological system is a mammal. The mammal is selected from humans or agriculturally important mammals such as cattle, horses, sheep or veterinary animals such as cats, dogs, rabbits or rodents, such as mice and rats.

The cancer cells are selected from the group consisting of breast cancer, ovarian cancer, basal-cell carcinoma, small-cell lung carcinoma, non-small cell lung carcinoma, squamous cell carcinoma, hepatocellular carcinoma, renal cell carcinoma, and multiple myeloma.

A method for evaluating the response of a biological system (e.g. cell, tissue, or human) exposed to a telomerase modulator comprising: (a) combining in a reaction vessel (1) the telomerase ribonucleoprotein enzyme complex from the subject bound to a solid support, (2) a first primer, which is suitable as a telomerase substrate, and (3) a plurality of nucleoside triphosphates to form a reaction mixture, and incubating the reaction mixture under conditions to extend the first primer in an extension reaction to produce an extension product; and (b) qualitatively or quantitatively detecting the extension product and correlating the amount of extension product with the amount of telomerase activity; (c) comparing the level of telomerase activity after administration of the modulator to the standard telomerase activity to determine the biological response of the system.

These and other objects and features of the invention will become more fully apparent when the following detailed description of the invention is read in conjunction with the accompanying drawings.

BRIEF DESCRIPTION OF THE DRAWINGS

FIG. 2 is a picture of a polyacrylamide gel showing the telomerase amplification products in A549 and HEK cell lines.

FIG. 5 is the sequence of human telomerase reverse transcriptase (SEQ ID NO:1).

DETAILED DESCRIPTION OF THE INVENTION

I. Definitions

Figure 1:
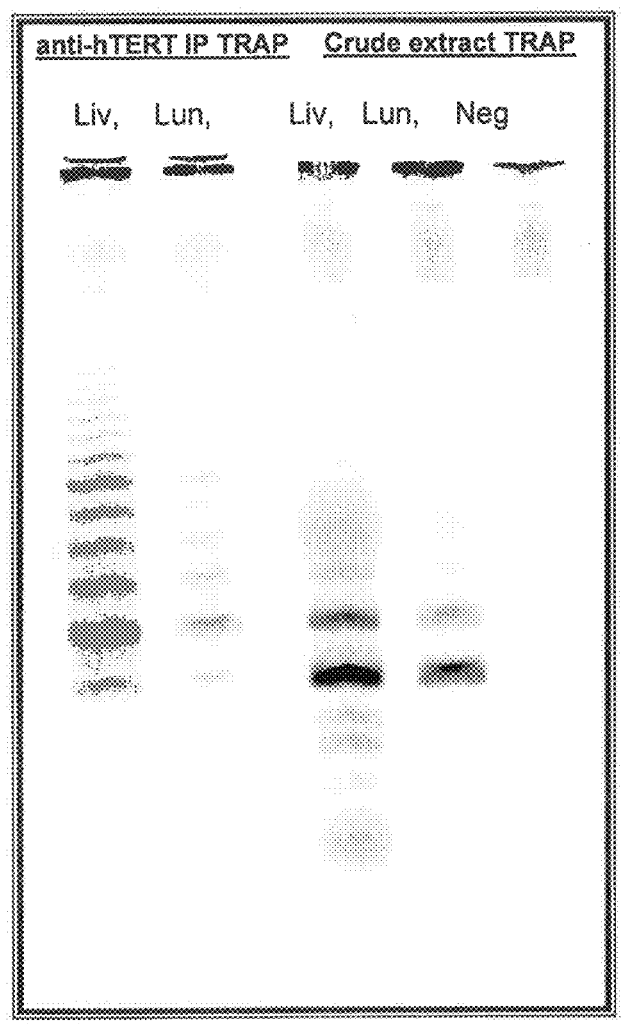
FIG. 1 is a picture of a polyacrylamide gel showing the telomerase amplification products in rat liver and lung tissue from a crude extract of cells and in the same tissues measured after the telomerase complex from the tissue was bound to beads with anti-telomerase antibody.

The terms below have the following meanings unless indicated otherwise.

A "mammalian biological system" refers to mammalian cells or tissue or a mammal. The cell or tissue extract may be obtained from mammals such as humans; agriculturally important mammals, such as cattle, horses, sheep; and/or veterinary mammals, such as cats, rabbits, rodents and dogs. The Mammal may be a human or agriculturally important mammals or veterinary mammals. Preferably the mammalian biological system is known to express telomerase reverse transcriptase.

A "cell extract or tissue extract" refers to the biological extract obtained from cells or tissues. In mammals, such cells may be selected from hair follicle cells, peripheral blood cells, cancer cells, buccal cells, skin cells or any other cells from the subject.

The "first primer which is suitable as a telomerase substrate" or "TS" is an oligonucleotide chosen to be recognized by the mammalian telomerase to be tested. If one is using the present method to determine the level of telomerase activity in a human subject, one employs a telomerase substrate recognized by human telomerase reverse transcriptase. Preferably when one employs a DNA polymerase based primer amplification step, the first primer suitable as a telomerase substrate should not comprise a complete telomeric repeat sequence to minimize primer dimer formation. For instance, a human telomerase substrate of the invention is oligonucleotide TS, which contains a sequence at its 3'end that is identical to five of the six bases of the human telomeric repeat but otherwise contains no complete telomeric repeat sequences.

A "second primer for amplification" comprises a sequence sufficiently complementary to a telomeric repeat and includes a primer that may contain one or more mismatched bases within the repeats which are complementary to the telomerase substrate extension product to which the primer is intended to hybridize. The number of mismatches that can be tolerated within this definition can vary depending upon the length and sequence composition of the primer, the temperature and reaction conditions employed during the PCR step. A "CX primer" is also called a "reverse primer" is composed of sequences complementary to imperfect telomeric repeats and one perfect repeat. For example the primer may be 5'-(CCCTTA)$_3$CCCTAA-3' (SEQ ID NO:4).

"Telomerase reverse transcriptase enzyme complex" comprises the telomerase reverse transcriptase enzyme, the telomerase RNA and other ancillary proteins which are necessary to make an active mammalian telomerase ribonucleoprotein complex. Without being limiting, an example of such ancillary proteins which may be present is the dyskerin protein.

An "anti-telomerase antibody" is an antibody that is able to bind the telomerase reverse transcriptase protein and allows the telomerase protein to retain its telomerase activity. The antibodies of the invention can specifically recognize and bind polypeptides that have an amino acid sequence identical to the amino acid sequence of human telomerase reverse transcriptase or fragments thereof, and allow the human telomerase to be active. The antibodies can specifically recognize and bind polypeptides that have the amino acid sequence set forth in FIG. 5, (SEQ ID NO:1) or fragments thereof. The antibodies can recognize and bind the sequence ARPAEEATSLEGALSGTRH or fragments thereof that comprise at least 10, at least 12 or at least 14 amino acids.

The anti-telomerase antibody is a "non-neutralizing antibody". It has been found that the telomerase enzyme complex does not need to be removed or eluted from the anti-telomerase antibody of the present invention in order for the telomerase enzyme to be active. A non-neutralizing antibody does not neutralize or inactivate the telomerase enzyme allowing the enzyme complex to have telomerase activity.

"Telomerase activity" is the processive activity of a telomerase reverse transcriptase protein in the presence of telomerase RNA. In particular, the processing activity of the telomerase is the addition of telomeric DNA repeats to a telomerase substrate per unit time.

A "telomerase modulator" is a compound that directly or indirectly either inhibits or activates the expression or activity of telomerase. A "telomerase modulator" may be a "telomerase inhibitor" or a "telomerase activator".

A "telomerase inhibitor" is a compound that directly or indirectly inhibits or blocks the expression or activity of telomerase. A telomerase inhibitor is said to inhibit or block telomerase if the activity of the telomerase in the presence of the compound is less than that observed in the absence of the compound. Preferably the telomerase is human telomerase. More preferably, the telomerase inhibitor is an hTR template inhibitor. An "hTR template inhibitor" is a compound that blocks the template region of the RNA component of human telomerase, thereby inhibiting the activity of the enzyme. For example, a telomerase inhibitor is GRN163L. (See U.S. Pat. No. 7,494,982 which is incorporated by reference herein)

A "cancer" is a malignant tumor. In particular, the cancer is a malignant tumor of epithelial-cell origin, that is, a malignant tumor that begins in the lining layer (epithelial cells) of organs. At least 80% of all cancers are carcinomas, and include breast cancer, both ductal and lobular carcinomas of the breast; ovarian cancer; basal-cell carcinoma, the most common non-melanoma skin cancer; squamous cell carcinoma, a common form of skin cancer and the most common type of lung cancer; hepatocellular carcinoma, the most common form of liver cancer; renal cell carcinoma, a malignant tumor located of the kidneys; and transitional cell carcinoma, a type of cancer that develops in the lining of the bladder, ureter, or renal pelvis. The cancer cells making up a carcinoma are referred to as "carcinoma cells." Also includes in the term "cancer" are cancers of the blood cells such as leukemias, lymphomas and myelomas.

All articles, books or journals referenced herein are incorporated herein in their entirety.

II. Generation of Antibodies and Binding of Telomerase Reverse Transcriptase

The present invention provides solid supports to which antibodies that are specifically immunoreactive with active human telomerase reverse transcriptase are bound. The antibodies include polyclonal and monoclonal antibodies, antibody fragments, single chain antibodies, humanized and chimeric antibodies.

The antibodies of the invention can specifically recognize and bind polypeptides that have an amino acid sequence that is substantially identical to the amino acid sequence set forth in FIG. 5 (SEQ ID NO:1), or an immunogenic fragment thereof or epitope on the protein defined thereby. The invention also provides anti-telomerase antibodies that recognize a conformational epitope (e.g. an epitope on the surface of the telomerase reverse transcriptase protein or a telomerase ribonucleoprotein). Likely conformational epitopes can be identified, if desired, by computer-assisted analysis of the telomerase protein sequence.

The antibodies of the present invention bind the human telomerase reverse transcriptase ribonucleoprotein, which forms part of an enzyme complex comprising the telomerase RNA, the telomere sequence, as well as any ancillary proteins necessary for processive activity of the telomerase reverse transcriptase complex. The antibodies of the present invention bind the telomerase reverse transcriptase in such a way that the processive activity of the enzyme is preserved when bound to the antibody. Preferably the antibodies when bound to a solid support bind to the telomerase complex in such a way that the telomerase complex has processive activity.

Peptides used to induce specific antibodies typically have an amino acid sequence comprising at least 8, at least 10, at least 12, or at least 14 consecutive amino acids of identity with the amino acid sequence of the protein of SEQ ID NO:1. The peptides used to induce the specific antibodies are typically from 10-25 amino acids or from 10 to 20 amino acids in length.

One example of the antibodies of the present invention are antibodies specific for the sequence ARPAEEATSLEGALSGTRH (SEQ ID NO:2) which corresponds to human telomerase reverse transcriptase (hTERT) amino acids 276 to 294 of SEQ ID NO:1. The antibodies of the present invention are antibodies specific to a peptide fragment that comprises at least 8-19, 10 to 19 amino acids, at least 12 to 19 amino acids, at least 14 to 19 amino acids of the sequence ARPAEEATSLEGALSGTRH (SEQ ID NO:2). The peptide sequence may further contain one or more cysteine or other residues at the N or C terminus of the peptide, for example to facilitate conjugation with other molecules to enhance an immune response in the animal generating antibodies. The antibodies of the present invention are antibodies specific to a peptide fragment that consists of ARPAEEATSLEGALSGTRH (SEQ ID NO:2) or CARPAEEATSLEGALSGTRH (SEQ ID NO:7).

In some cases conjugation of the peptide to a larger molecule may be necessary or desirable for antibody development. Examples of such immunogenic proteins include, but are not limited to, keyhole limpet hemocyanin, serum albumin, bovine thyroglobulin, and soybean trypsin inhibitor. Typically a peptide is conjugated to a carrier protein through a stable covalent bond. The point of conjugation can be at the N or C terminus or in the middle of a peptide. A cysteine is usually used at the point of conjugation with the immunogenic protein. If the desired hTERT peptide sequence does not contain a cysteine residue, a cysteine residue may be added to the peptide sequence at the N or C terminus of the peptide to allow conjugation to the immunogenic peptide.

The antibodies of the invention can exhibit a specific binding affinity for human telomerase reverse transcriptase with a kD of at least about $10^7$, $10^8$, $10^9$ or $10^{10} M^{-1}$ and may be polyclonal, monoclonal, recombinant or otherwise produced.

The antibodies of the invention may be any isotype, e.g. IgM, IgD, IgG, IgA and IgE, with IgG, IgA and IgM preferred.

1. Polyclonal Antibodies

The anti-telomerase antibodies may comprise polyclonal antibodies (also known as a polyclonal mixture of antibodies comprising anti-telomerase antibodies). Methods of preparing polyclonal antibodies are known. For production of the anti-hTRT antibodies, hosts such as goats, sheep, cows, guinea pigs, rabbits, rats or mice may be immunized by one or more injections with hTRT protein or any portion, fragment or peptide thereof which retains immunogenic properties. In selecting telomerasc polypeptides for antibody induction, one need not retain biological activity; however the protein fragment or peptide must be immunogenic. Immunogenicity can be determined by injecting a polypeptide and adjuvant into an animal (e.g. a rabbit) and assaying for the appearance of antibodies directed against the injected polypeptide. Typically the peptide and/or adjuvant will be injected in the mammal by multiple subcutaneous or intraperitoneal injections. Examples of adjuvants which may be employed include Freund's complete adjuvant and MPL-TDM adjuvant (monophosphoryl Lipid A, synthetic trehalose dicorynomycolate).

Preferably the peptides used to generate the antibody are taken from portion of the telomerase enzyme where binding of the antibody to the telomerase will not affect the processive activity of the telomerase. Antibody generated can be tested by the described methods to determine whether telomerase bound to the antibody retains processive activity.

The antibodies produced by the host can be precipitated, isolated and purified by routine methods, including affinity purification. For example IgG antibodies can be purified using bacterial proteins, such as, Protein A (*Staphylococcus aureus*) and Protein G (from group G streptococci) based on their ability to bind to the Fc region of the immunoglobulin IgG. Purification of an antibody specific for a particular antigen and free of contamination from other immunoglobulins can be accomplished by immobilizing the antigen on a column so that only antibodies binding specifically to the immunization antigen are isolated.

2. Monoclonal Antibodies

The anti-telomerase antibodies may be monoclonal antibodies. Monoclonal antibodies may be prepared by using hybridoma methods, such as those originally described by Koehler and Milstein (Nature 256:495 [1975], the human B-cell hybridoma technique (Kosbor et al., 1983, Immunol. Today 4:72,) and EBV-hybridoma technique (Cole et al., Monoclonal Antibodies and Cancer Therapy, Alan R Liss Inc. New York N.Y. pp 77-96 [1985]) or other means known in the art.

For example, production of non-human monoclonal antibodies, e.g. murine, rabbit, sheep, the mammal is immunized with a preparation containing telomerase fragments. After the appropriate time, the spleens or lymph nodes of the animals are excised and individual spleen cells or lymph node cells are isolated. The lymphocytes are then fused with an immortalized cell line using a suitable fusing agent, such as polyethylene glycol, to form a hybridoma cell. Thereafter, the cells are clonally separated and supernatants of each clone (e.g. hybridoma) are tested for the production of an appropriate antibody specific for the desired region of telomerase. Techniques for producing monoclonal antibodies are well known in the art.

Solid Supports.

The anti-telomerase antibody is bound to a solid surface or support. Many methods for immobilizing antibodies to a variety of solid surfaces are known in the art. For example, the solid surface may be a membrane (e.g. nitrocellulose), a microtiter dish (e.g. polyvinylchloride (PVC), polypropylene, or polystyrene) a test tube (glass or plastic) a dipstick (e.g. glass, PVC, polypropylene, polystyrene, latex and the like) a microcentrifuge tube or a glass, agarose, magnetic or plastic bead. The antibody may be covalently bound or non-covalently bound. The antibody may be bound through specific or non-specific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinylbutyrate), polyvinylidene difluoride (PVDF), silicones, polyformaldehyde, cellulose, cellulose acetate, nitrocellulose and the like. Other materials which may be employed include paper, glass, ceramics, metals metalloids semiconductive materials, cements or the like. In addition substances that form gels, such as proteins (e.g. gelatins) lipopolysaccharides, silicates, agarose and polyacrylamides can be used. Where the solid surface is porous, various port sizes may be employed depending on the nature of the system. The solid support may be agarose beads or superparamagnetic beads. It is contemplated that the solid support may be agarose beads in a microtip column, such as the Phytip column commercially available from PhyNexus (San Jose Calif.).

If covalent bonding between the antibody and the solid support is desired, the surface of the solid support will usually be polyfunctional or be capable of being polyfunctionalized. Functional groups which may be present on the surface and used for linking can include carboxylic acids, aldehydes, amino a groups, cyano groups, ethylene groups, hydroxyl groups, mercapto groups, and the like. The manner of linking antibodies to various surfaces is known.

In addition to covalent bonding, various methods for non-covalently bonding an antibody to a solid support can be used. Noncovalent bonding is typically adsorption of the antibody to the surface. For example, the surface is designed such that it specifically binds the antibody but does not significantly bind other proteins. For example, the surface may be treated with protein A (*Staphylococcus aureus*) or protein G which specifically bind the FC region of IgG antibodies.

III. Measurement Of Activity

The invention is directed to a method for the detection or measurement of telomerase activity as well as reagents suitable therefore. The activity may be detected by a direct (no amplification of products) assay or by an indirect assay which typically measures amplification products or amplified signals. There are several variations on both types of assay.

For example, for the direct method of detecting telomerase activity, one first prepares a cell or tissue extract; preferably using a detergent based extraction method. Suitable buffers include M-Per buffer. Then the cell or tissue extract or an aliquot of the cell or tissue extract is placed in a reaction mixture comprising a first primer which acts as a telomerase substrate, a buffer compatible with telomerase activity and a plurality of nucleoside triphosphates. The particular telomerase substrate chosen may vary depending on the type or origin of the telomerase activity for which one is testing. The telomerase activity expressed by one mammal may differ with respect to substrate specificity from that expressed by another mammal. Consequently, if one is using the method to determine the effect of a telomerase modulator on a human, one employs a telomerase substrate that is adequately recognized by human telomerase. Vertebrate (hence human) telomerase adds repeats of sequence 5'-TTAGGG-3'. Therefore the telomerase substrate must be a DNA sequence which allows the addition of TTAGGG repeats. For humans, a first primer DNA sequence with a 3' end sequence of 5'-GTT-3' has been found to allow processive addition of "AG(GGTTAG)$_n$," repeats, such as, for example, a first primer DNA sequence with a 3' end sequence of 5'-GTT-3'

Generally the first primer which is suitable as a telomerase primer is covalently labeled, covalently attached to a ligand or covalently bound to an anchor group. The extension reaction of the first primer is stopped and the reaction mixture is transferred to a plate or column. For example, when the first primer is bound to biotin, the plate may be coated with avidin or streptavidin. The first primer is captured by the binding of the anchor group to the plate or column. During the extension reaction, one or more of the nucleoside triphosphates are labeled either fluorescently or radioactively. Once the first primer is bound to the solid surface, the level of label (either fluorescence or radioactivity) is measured to give a measurement of the level of processive activity of the telomerase enzyme complex.

The TRAP assay is a standard indirect method for measuring telomerase activity in a cell extract system (Kim et al., *Science* 266:2011, 1997; Weinrich et al., *Nature Genetics*

17:498, 1997). Briefly, this assay measures the amount of nucleotides incorporated into elongation products (polynucleotides) formed by nucleotide addition to a labeled telomerase substrate or primer after PCR amplification of the initial telomerase-extended substrate. This method is described in detail in U.S. Pat. Nos. 5,837,453, 5,863,726 and 5,804,380, as well as in U.S. Pat. Nos. 5,629,154 and 5,648,215, which are incorporated herein in their entirety. The use of the TRAP assay in testing the activity of telomerase inhibitory compounds is described in various publications, including WO 01/18015. In addition, the following kits are available commercially for research purposes for measuring telomerase activity: TRAPeze™ XK Telomerase Detection Kit (Millipore; Billerica Mass.) and TeloTAGGG Telomerase PCR ELISA plus (Roche Diagnostics, Indianapolis Ind.).

The telomerase substrate extension reaction is conducted similarly to that described for the direct assay. Subsequently, the second primer complementary to the telomere sequence is extended which serves to amplify the signal produced by the presence of telomerase activity in a sample (extended telomerase substrates) by producing a second signal (extended primers). The reaction for extension of the second primer can be conducted in the same reaction vessel as the first primer extension by the telomerase. There is no need to isolate the extended first primers prior to the second primer extension. Alternatively the extended first primers may be removed prior to the polymerase chain reaction.

The second primers can be extended by any means that requires the presence of extended telomerase substrates for primer extension to occur; preferred means are mediated by a template-dependent DNA or RNA polymerase, a template-dependent DNA ligase, or a combination of the two. With these means, if telomerase activity is present in the sample, an extended telomerase substrate is formed and then hybridizes to a primer, providing a substrate for either DNA or RNA polymerase or DNA ligase to produce a primer extension product.

When one employs a DNA polymerase-based primer extension step, the present method requires that the first primer suitable as a telomerase substrate not comprise a telomeric repeat sequence. The human telomerase adds repeats of sequence 5'-TTAGGG-3'. Thus, if one is using the indirect method to assay for human telomerase activity, the telomerase substrate should be a human telomerase substrate lacking the sequence 5'-TTAGGG-3'. This requirement for the first primer suitable as a telomerase substrate to lack telomeric repeat sequences arises out of the second reaction of the indirect method, the non-telomerase-mediated primer extension reaction. In this reaction, an oligonucleotide primer that hybridizes only to extended telomerase substrates is added to the reaction mixture under conditions such that, if extended telomerase substrates are present, the primer binds to the extended substrates and is then extended by enzymatic action. Because telomerase can extend the telomerase substrate only by the addition of telomeric repeats, the second oligonucleotide primer will necessarily comprise a sequence complementary to a telomeric repeat. If the first primer suitable as a telomerase substrate sequence employed in the telomerase extension reaction comprised a telomeric repeat, then the second primer employed in the primer extension reaction could hybridize to unextended telomerase substrate, resulting in false positive results.

Once a primer extension product has formed, one can disassociate (typically by heating, but one could also use an enzyme or chemical process, such as treatment with helicase) the extended primer from the extended substrate. If additional primer and primer extension reagent is present in the sample, then a new primer/extended telomerase substrate complex can form, leading to the production of another extended primer. One can repeat the process of primer extension and denaturation several to many times, depending upon the amount of signal desired. Typically, primer extension and denaturation of extended primer/extended telomerase substrate complexes will be performed at least 5, 10, 15, 20, 25 to 45 or more times, from 20 to 38 times, from 25 to 35 times. Moreover, if a second primer complementary to the 3'-end of the extended primer is present in the reaction mixture, one can increase the signal (both extended primer and also additional extended telomerase substrate) dramatically. Unextended telomerase substrate still present in the reaction mixture during the primer extension step can function as such a second primer.

Those of skill in the art will recognize that if the primer extension reagent is a DNA polymerase, and a second primer is present, one has the requisite components for a polymerase chain reaction, more fully described in U.S. Pat. Nos. 4,683,195; 4,683,202; and 4,965,188, provided the appropriate buffer and nucleoside triphosphates are present in the reaction mixture. PCR amplification is a preferred mode for conducting the primer extension reaction step of the present invention and dramatically increases sensitivity, speed, and efficiency of detecting telomerase activity as compared to the conventional assay.

The reaction mixture may be separated by gel electrophoresis and the pattern and amount of bands visualized. Because telomerase stalls and can release the DNA after adding the first G in the 5'-TTAGGG-3' telomeric repeat, the characteristic patter of products on the gel is a six nucleotide ladder of extended oligonucleotide substrates.

Alternatively the reaction mixture can be monitored during the polymerase chain reaction in real time for the incorporation of radioactive or fluorescent signal to monitor the amount of double stranded DNA generated. This method is generally referred to as real-time PCR or Q-PCR.

PCR normalization of the intensity of the telomerase ladder to that of the internal standard permits the assay to become linear so that accurate comparisons between samples can be made, as is described in the Examples section below. A weak signal resulting from the internal standard relative to that in other samples could indicate limiting PCR conditions, thus allowing the practitioner to choose to repeat the assay under non-limiting conditions, for example, by providing higher polymerase levels. The inclusion of the internal standard also immediately identifies potentially false negative samples.

One means for obtaining quantitative information is the use of a PCR control oligonucleotide template added to each reaction mixture in a known amount. An illustrative PCR control oligonucleotide comprises, in 5'-3' order, a telomerase substrate sequence, a spacer sequence (which can be any sequence of nucleotides or length and can alter spacing of the ladder produced by electrophoresis of reaction products produced from telomerase containing samples), a telomeric repeat sequence (typically present in multiple, i.e., 2 to 50, copies), and a sequence complementary to the primer used in the assay (and so which may simply be a portion of the telomeric repeat sequence). Of course, an oligonucleotide complementary to the control sequence defined above can also serve as the control sequence, and a double-stranded control nucleic acid can also be employed.

Alternatively, one can add a PCR control nucleic acid of any sequence to the reaction mixture in known amounts and amplify the control with primers which can be the same as or different from those used to amplify the extended telomerase substrate. The control oligonucleotide and/or the primers used to amplify the control oligonucleotide can be labelled identically to or differently from the label used to detect the telomerase extension products. Use of an internal control not only facilitates the determination of whether the assay was conducted properly but also facilitates quantitation of the telomerase activity present in the sample. The detailed protocol for conducting TRAP assays using primer and internal control is described in U.S. Pat. Nos. 5,629,154, and 5,863,726 which are incorporated herein in their entirety.

Moreover, a variety of different types of oligonucleotides can be used in telomerase activity assays. While the discussion above and Examples below illustrate assay methods with results obtained using oligodeoxyribonucleotide telomerase substrates and primers with DNA polymerase, the activity assay used in the present invention is not so limited. Thus, one can employ oligoribonucleotides or oligonucleotides that comprise one or more modified (i.e., synthetic or non-naturally occurring) nucleotides in the telomerase assay. In similar fashion, one can employ an RNA polymerase to extend a primer or to copy an extended telomerase substrate. These and other variations of the present method will be apparent to those of skill in the art upon consideration of this description of the invention.

The intensity of the telomerase product generated may also be normalized relative to cell number, or to a control molecule such as, for example, RNA or total protein so that comparisons between samples can be made. This provides correction for the extraction efficiency of telomerase from the cellular extract allowing different samples to be compared. The activity of the telomerase may thus be expressed as a value relative to cell number, to protein amount or RNA amount. Where ribosomal RNA serves as the normalization control, the ribosomal RNA can be determined by a PCR reaction using primers directed to the 18S ribosomal RNA. Alternatively the amount of mRNA in the cell extract may be determined by measuring the mRNA for genes specifically expressed in the cells or interest or housekeeping genes.

The level of activity measured by the telomerase assay after exposure to a telomerase modulator can be compared to the telomerase activity prior to exposure to the telomerase modulator. A difference in activity is typically observed when there is at least a 10% increase, at least a 50% increase, at least a 2 fold increase, at least a 4 fold increase or at least a 6 fold increase in activity after exposure to a telomerase activator. A difference is activity is observed when there is typically less than 90% of the activity, less than 80% of the activity, less than 70% of the activity or less than 50% of the activity after exposure to a telomerase inhibitor.

The invention provides new ways of determining how many telomeric repeats are added to the telomere substrate and how many copies of each number of telomeric repeats are present in the reaction mixture by considering how much signal from the different sized telomerase repeat amplification products are present in the reaction mixture and comparing those levels to the expected level.

The following examples are offered by way of illustration and not by way of limitation.

EXAMPLES

Example 1

Measuring Telomerase (TRAP) Activity

A polyclonal mixture of anti-telomerase antibody generated by inoculating sheep with the peptide ARPAEEATSLE-GALSGTRH was obtained from Cohen (Science vol 315 pp 1850, 30 Mar. 2007). Briefly, for immunization of sheep, the synthetic peptide antigen was conjugated to Diptheria toxoid with maleimidocaproyl-N-hydroxysuccinimide as a linker. The sheep were immunized and bled. An affinity column of immobilized antigenic peptide was prepared through covalent reaction of the $NH_2$—terminus with beads bearing N-hydroxysuccinimide esters. The antibody serum from the sheep was added to the antigenic column. The antibody was eluted from the column in 1 mL fractions of glycine and concentrated. The purified antibody displayed a $K_d$ of 20±5 nM at 2° C.

10 ug of purified anti-telomerase antibody was rotated in solution at 10 rpm at 4° C. for 30 min. 1 mM phenylmethylsulfonyl fluoride (PMSF) was added to the antibody. 40 uL of protein G-Dynabeads® (Invitrogene, San Diego Calif.) (80 uL of 50% suspension) was added to the antibody and the suspension rotated at 10 rpm at 4° C. for 1 hr to allow the antibody to become bound to the Dynabeads.

Tissue extract preparation: Rat liver and lung tissue were flash frozen and kept in −80 C. Frozen tissue was lysed in M-Per buffer lysis buffer (Pierce Thermo Fisher Scientific, Rockford Ill.) with 1 mM PMSF after 10 seconds of homogenization. The sample was kept on ice for 20 min. and then centrifuged at 10,000×g for 30 minutes an Eppendorf Centrifuge 5417R (Westbury N.Y.). The supernatant was transferred to a fresh tube or flash frozen in dry ice/methanol.

Cultured cell lines extract preparation: Cells were washed with phosphate buffered saline (PBS) and trypsinized and counted. Cell pellets were made (1 million cells/pellet) and stored in −80° C. Cell lysate was made from $10^6$ cell/100 uL by lysing in M-Per lysis buffer (Pierce Thermo Fisher Scientific, Rockford Ill.), on ice for about 1 hr. The sample was centrifuged at 10,000×g for 20 minutes an Eppendorf Centrifuge 5417R (Westbury N.Y.). The supernatant was transferred to a fresh tube or flash frozen in dry ice/methanol. 0.2 mL of cell or tissue extract were used per immunoprecipitation.

40 uL of Dynabeads-ProG® beads per sample were washed with 0.5 mL lysis buffer. 5-10 ug of purified anti-telomerase antibody was added and the solution rotated at 10 rpm at 4° C. for 30 min (with PMSF, 1 mM). The anti-telomerase antibody bound to the Dynabeads-ProG® beads was placed in a tube on a magnet for 1 min and the supernatant discarded by aspiration with a pipette while the tube remained on the magnet. The tube was removed from the magnet, the beads were washed 2× by adding 1 mL of lysis buffer.

0.2 mL of cell or tissue extract were added to the anti-telomerase antibody bound Dynabeads-ProG® beads and the antibody bound Dynabeads-ProG® beads and cell or tissue extract suspension was rotated at 10 rpm at 4° C. for 1 hr. The immunoprecipitation tubes then were placed on a magnet stand for 1 min and the supernatant discarded by aspiration with pipette while the tube remained on the magnet. The tube was removed from the magnet, the beads were washed once by adding 1 mL lysis buffer and then twice with ice-cold 1×TRAP buffer. After each wash, the tube was placed on the magnet for 1 min and the supernatant discarded by aspiration with a pipette while the tube remained on the magnet.

50 uL of TRAP reaction mix (as the following table) was added into the tubes containing beads-anti-telomerase antibody-telomerase complex and the beads were resuspended in the TRAP reaction mix. The tubes were then immediately put in the PCR machine for the TRAP reaction as follows.

10×TRAP Buffer:

| Tris-HCl pH 8.3 | 200 mM |
|---|---|
| MgCl2 | 15 mM |
| KCl | 630 mM |
| Tween 20 | 0.5% |
| EGTA | 10 mM |
| BSA | 1 mg/ml |

Primers:

Cy5-TS(AAT CCG TCG AGC AGA GTT)5'   (SEQ ID NO: 3)

ACX(GCGCGGCTTACCCTTACCCTTACCCTAACC)   (SEQ ID NO: 6)

Taq polymerase is AmpliTaq DNA Polymerase, Applied Biosystems, and dNTP from Invitrogen

| TRAP reaction mix (per sample) | | | |
|---|---|---|---|
| | Stock Conc. | uL, per rxn | Final Conc. |
| 10x TRAP buffer | | 5 | 1x |
| dNTP | 2.5 mM | 1 | 50 uM |
| Cy5-TS | 0.5 mg/ml, 83 uM | 0.1 | 1 ng/μLl |
| ACX | 0.1 mg/ml, 11 uM | 1 | 2 ng/μL |
| Taq polymerase | 5 U/μL | 0.4 | 0.04 U/μL |
| H2O | | 37.5 | |
| total | | 50 | |

The telomere extension and PCR amplification was conducted as follows:
a. 30° C. for 30 minutes
b. 28 to 33 cycles of the following 3-step reaction:
   94° C. for 30 seconds
   60° C. for 30 seconds
   72° C. for 1 minute
c. 72° C. for 4 minutes
d. Hold at 4° C.

The TRAP reaction products were run on an polyacrylamide gel. 35 μL of each TRAP reaction was loaded onto a polyacrylamide gel (15% acrylamide/1% N,N'-methylene-bis acrylamide)(BioRad Lab, Inc. Hercules Calif.). The intensity of the specific ladder bands on the gel was measured for quantitation of telomerase activity.

FIG. 1 is a picture of a polyacrylamide gel and is a comparison of the relative telomerase activity of the analysis of the TRAP reaction products using telomerase isolated from rat liver or lung tissues by the usual method and telomerase from the same tissues isolated and bound by the anti-telomerase antibodies. It was found that it was possible to specifically isolate active telomerase complex using the antibodies bound to a solid support and that the bound telomerase was active and gave a cleaner and stronger signal (less background smearing, more intense bands, and more bands (greater processivity)) compared to the standard assay with crude extracts. It was also clear that the signal obtained with the bound telomerase could be more readily quantified than that obtained from the crude telomerase extract.

FIG. 2 is a picture of the TRAP reaction products as run on a polyacrylamide gel and shows that the telomerase from different cell lines, (A549 (Human lung adenocarcinoma epithelial cell line with high telomerase activity) and HEK (Human Epidermal Keratinocyte, primary cell line with low telomerase activity) could be isolated using the solid support bound antibody and that the isolated telomerase was active and could be readily quantified.

These results showed that the anti-hTERT antibody can be used for immuniprecipitation of active human telomerase from both cell lines and tissue extract. The antibody did not block the telomerase catalytic domain and the TRAP assay could be directly performed on beads. There did not need to be an additional step of eluting the telomerase from the beads prior to conducting the TRAP assay.

Example 2

Telomerase Activity Measurement by Rabbit Anti-hTERT Antibody

A second and third polyclonal mixture of anti-telomerase antibody was made by inoculating rabbits and a sheep with a construct comprising keyhole limpet hemocyanin linked to the N terminus of the peptide (H)-CARPAEEATSLEGALS-GTRH-(NH$_2$) (SEQ ID NO:7). The key-hole limpet hemocyanin (KLH) was activated with succinimidyl 4-[N-maleimidomethyl]cyclohexane-1-carboxylate (SMCC) (Pierce Thermo Fisher Scientific, Rockford Ill.) in 0.1 M sodium phosphate buffer (pH 7.5). the excess SMCC was removed by dialysis (molecular weight cut off 10,000) in sodium phosphate buffer (0.1 M, pH 6.5). Then the KLH was conjugated to the peptide via the Cys at the N-terminus in sodium phosphate buffer (0.1 M, pH 6.5). The excess peptide is removed via dialysis in sodium phosphate buffer (0.1 M, pH 6.5). The resulting conjugated peptide is dried down by lyophilization.

The animals were initially inoculated with the peptide construct emulsified in Freund's Complete Adjuvant by Covance's commercially available procedure (Denver, Pa.). Freund's Incomplete Adjuvant was used for all subsequent injections. The animals were bled and the immunoglobulin fraction collected. The rabbit antiserum was protein A/G purified by Covance's commercially available procedure (Denver, Pa.).

HEK293 cells were lysed ($10^6$ cells in 100 uL M-Per lysis buffer) 1 hr on ice. The cells were centrifuged at 14K, 4° C. for 30 min. The supernatant/extract was placed in fresh tubes for immunoprecipitation and TRAP assay.

To a diluted extract containing about $10^5$ cells in 100 uL, was added about 5-10 ug of rabbit anti-telomerase protein G purified antibody obtained from Covance. This was incubated 2 hr at 4-6° C. with 200 RPM shaking in a bench top thermo incubator. Dynabeads-ProG® beads were washed by 2×1 mL M-Per buffer and then brought back to the original volume in PBS. 20 uL of washed beads were added to the cell extract with anti-telomerase antibody prepared as above and incubated for 2 hr at 4-6° C. with shaking at 600 rpm. The immunoprecipitation tubes were placed on a magnet stand for 1 min and the supernatant discarded by aspiration with pipette while the tube remained on the magnet. The tube was removed from the magnet, the beads were washed once by adding 1 mL lysis buffer and then twice with ice-cold 1×TRAP buffer. The tubes were placed on the magnet for 1 min and the supernatant discarded by aspiration with a pipette.

While the tubes remained on the magnet stand 50 uL of TRAP mix without Taq polymerase was immediately added to the beads and the beads were resuspended after taking the tube off the magnet. The reaction was then incubated at 30° C. for 30 minutes. The tubes then put back on magnet stand.

In one case, the supernatant from the reaction was removed to PCR tubes and 0.4 uL Taq polymerase was added to the PCR tubes. 28 cycle of PCR as previously described was followed for amplification of the telomerase products.

In the second case, the full TRAP reaction mix with Taq was added to the remaining beads (after supernatant removal) in the immunoprecipitation tubes, resuspended and transferred to a new PCR plate. The TRAP reaction was run as previously described without separation of the supernatant from the beads.

The activity of telomerase captured by the rabbit anti-hTERT and Dynabeads-ProG® was measured by either (1) 1-step TRAP, TRAP assay on Dynabeads-ProG®/immuno complex or (2) by a 2-step TRAP: substrate extension on Dynabeads-ProG®/immuno complex and following by PCR amplification of the substrate extension products. Both reaction products were run on polyacrylamide gel as well as in the microfluid LabChip.

The activity of telomerase captured by the rabbit anti-hTERT and Dynabeads-ProG®) beads (Invitrogene, San Diego Calif. measured by 1-step TRAP, TRAP assay on Dynabeads-ProG®/immuno complex, and/or by 2-step TRAP, substrate extension on Dynabeads-ProG®/immuno complex and following by PCR amplification of the substrate extension products. The TRAP reaction products were the either run on an polyacrylamide gel or run in the LABCHIP® GX microfluidics system (Caliper Life Sciences, Mountainview, Calif.) by preparing the DNA chip according to the manufacturer's instructions and injecting the of Dye/Gel mixture into the microfluidic chip and loading 50 uL of DNA MARKER™ (Caliper Life Sciences, Mountainview, Calif.) to the chip. The chip was placed in the machine and 25 uL of TRAP reaction product were run according to the manufacturer's instructions.

Figures 3A, 3B:
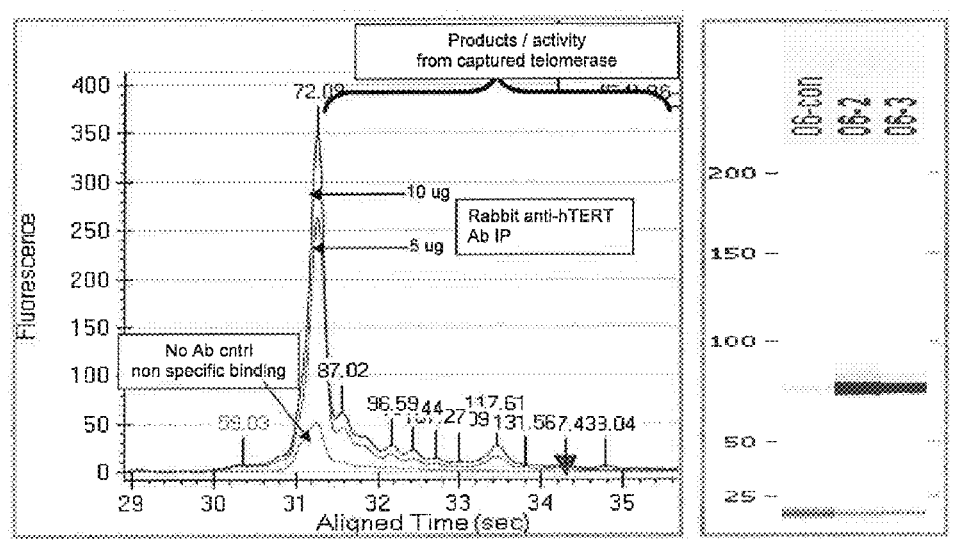
FIG. 3A is a graph of the level of telomerase amplification products obtained from telomerase captured by either 10 ug or 5 ug of rabbit anti-telomerase antibody bound to beads.
FIG. 3B is a picture of a polyacrylamide gel showing the telomerase amplification products.

FIGS. 3A and 3B show that it did not matter whether the reaction was run as a one step trap assay or as a two step trap assay, the trap reaction products were easily measured.

Example 3

Human bone marrow tissue (frozen pellets after Ficoll clean-up) and human peripheral blood mononuclear cells (PBMCs) were extracted by M-Per buffer ($10^6$ cell/100 uL) on ice for 1 hr and centrifuged at 10,000×g for 20 minutes. The supernatant was collected for immunoprecipitation and activity assessment.

40 uL of Dynabeads-ProG® per sample washed with 0.5 mL lysis buffer. 5-10 ug of Rabbit anti-hTERT antibody was added and the samples rotated at 10 rpm at 4 C for 30 min (with PMSF, 1 mM). The anti-hTERT antibody bound to the Dynabeads-ProG® was placed in a tube on a magnet for 1 min and the supernatant discarded by aspiration with pipette while the tube remained on the magnet. The tube was removed from the magnet, the beads were washed 2× by adding 1 mL of lysis buffer.

0.1 mL of cell or tissue extract were added to the anti-hTERT antibody bound Dynabeads-ProG® and the antibody bound Dynabeads-ProG® and cell or tissue extract suspension was rotated at 10 rpm at 4° C. for 1 hr. The immunoprecipitation tubes were placed on a magnet stand for 1 min and the supernatant discarded by aspiration with pipette while the tube remained on the magnet. The tube was removed from the magnet, the beads were washed 1× by adding 1 mL lysis buffer, 2× of ice-cold 1×TRAP buffer. The tube was placed on the magnet for 1 min and the supernatant discarded by aspiration with a pipette while the tube remained on the magnet.

50 uL of TRAP reaction mix as described in the previous example was added into the tubes containing IP complex (Ab-telomerase complex-Beads) and the beads resuspended in the TRAP reaction mix. The tubes were immediately put in PCR machine for the TRAP reaction as previously described. The TRAP reaction products were run on an polyacrylamide gel. 35 μL of each TRAP reaction was loaded onto a polyacrylamide gel (15% acrylamide/1% N,N'-methylene-bis acrylamide)(BioRad Lab, Inc. Hercules Calif.). The intensity of the specific ladder bands on the gel was measured for quantitation of telomerase activity.

Figure 4A:
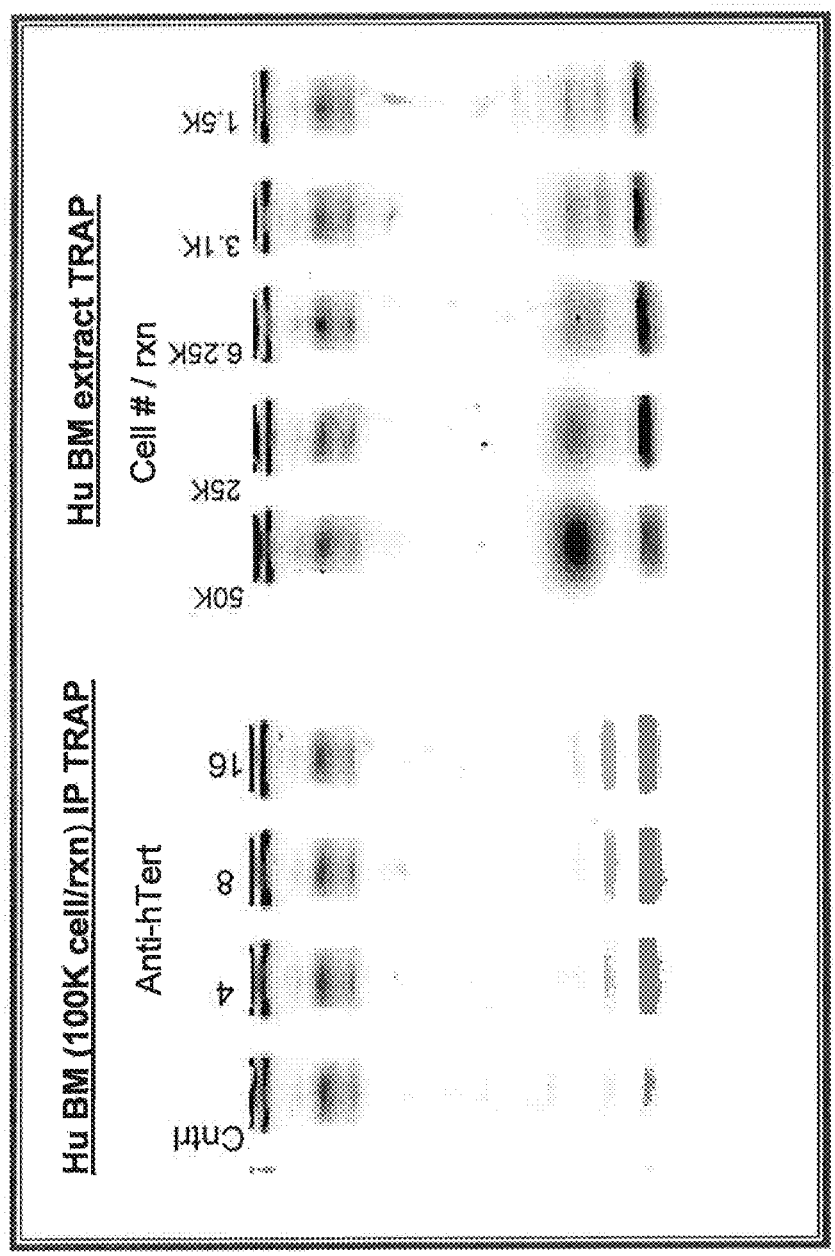
FIG. 4A is a picture of a polyacrylamide gel showing the telomerase amplification products of whole cell extracts from human bone marrow (HuBM) compared to the extract of $10^5$ cells bound to beads containing anti-telomerase antibody (IP).
Figure 4B:
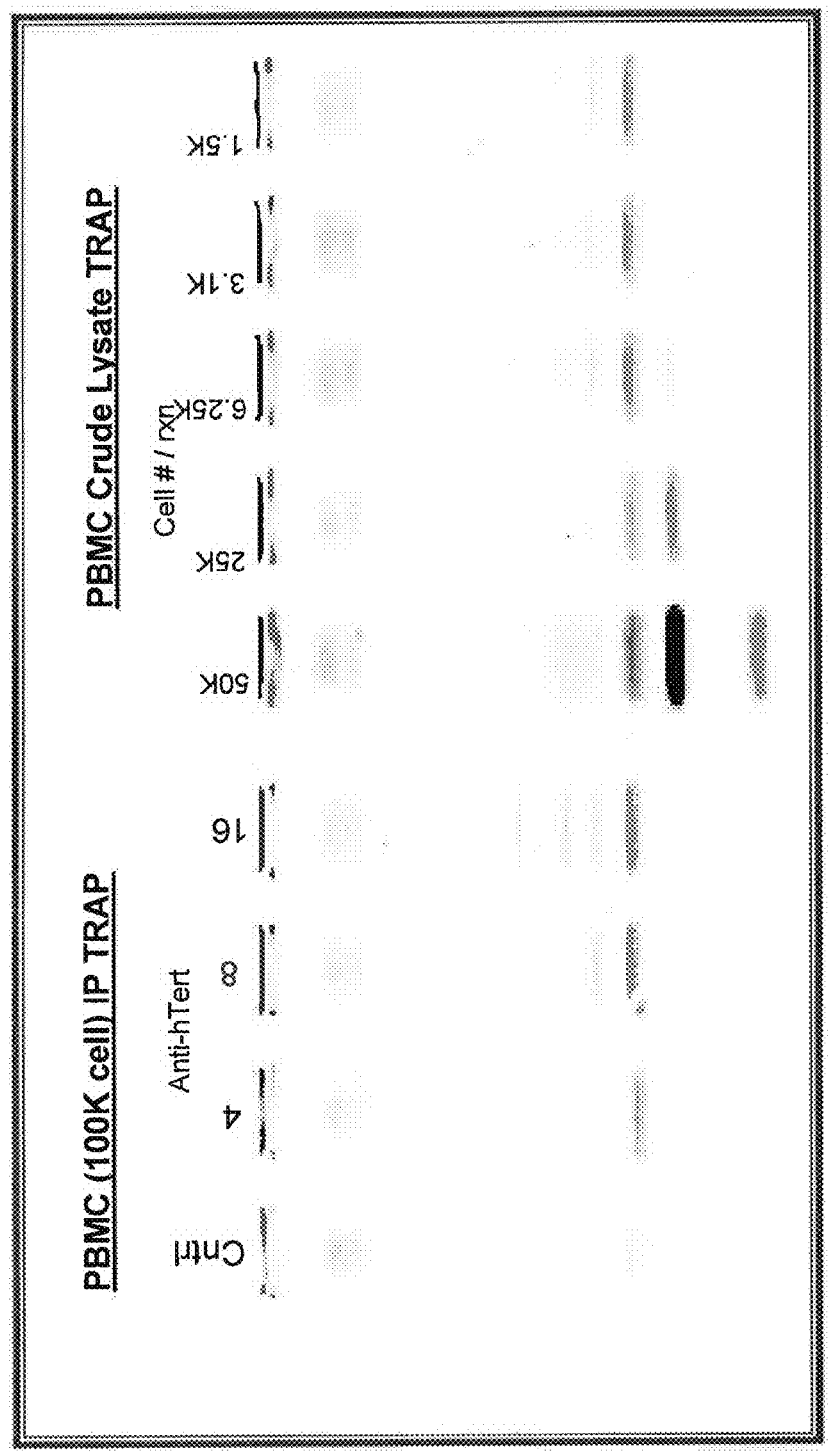
FIG. 4B is a picture of an polyacrylamide gel showing the telomerase amplification products of whole cell extract of $10^5$ cells from human peripheral blood mononuclear cells (PBMCs) compared to the extracts bound to beads containing anti-telomerase antibody (IP).

FIGS. 4A and 4B are pictures of the TRAP products as run on a polyacrylamide gel and shows that the telomerase from human bone marrow tissue and PBMC could be isolated using the solid support bound antibody and that the telomerase so isolated was active. The figure also shows that a larger amount of cell extract mixed with the anti-telomerase antibody and bound to the beads would result in a clearer polyacrylamide gel of the trap products. Therefore, this provides a method were the telomerase activity of a larger cell extract can be measured without introducing a high background obscuring the results.

Although the invention has been described with respect to particular embodiments and applications, those skilled in the art will appreciate the range of applications and methods of the invention disclosed herein.

What is claimed as the invention is:

1. A method for detecting a presence or an amount of telomerase activity, comprising:
   (a) combining in a reaction vessel (1) an active telomerase ribonucleoprotein enzyme complex bound to a solid support by a non-neutralizing anti-telomerase antibody that is specific for the peptide sequence ARPAEE-ATSLEGALSGTRH (SEQ ID NO:2), (2) a first primer, which is suitable as a telomerase substrate, and (3) a plurality of nucleoside triphosphates to form a reaction mixture, and incubating the reaction mixture under conditions to extend the first primer to produce an extension product; and
   (b) qualitatively or quantitatively detecting the extension product and correlating the detection with the presence or amount of telomerase activity.

2. The method of claim 1 wherein the antibody is a polyclonal mixture of antibodies specific for telomerase ribonucleoprotein enzyme complex.

3. The method of claim 1 wherein the first primer is labeled.

4. The method of claim 3 wherein the label is selected from the group consisting of a radioactive molecule, a fluorescent molecule, a phosphorescent molecule, a ligand for a receptor, and anchor group selected from biotin, avidin or streptavidin.

5. The method of claim 4 further comprising a step wherein the extension products are immobilized on a solid phase via an anchor group.

6. The method of claims 5 wherein the anchor group is biotin and the solid phase is coated with avidin and/or streptavidin.

7. The method of claim 1 further comprising a step wherein the extension products are amplified to produce amplification products and qualitatively or quantitatively detecting the amplification products to qualitatively or quantitatively detect the extension product.

8. The method of claim 7 wherein the extension products are amplified by adding to the reaction mixture a second primer comprising a sequence complementary to a telomeric repeat and extending the second primer to produce amplification products.

9. The method of claim 8 wherein the second primer comprises a non-telomeric repeat sequence at the 5'-end of said primer.

10. The method of claim 8 wherein the second primer is 5'-CCCTTACCCTTACCCTTACCCTAA -3'(SEQ ID NO:4), 5-GCGCGGCTAACCCTAACCCTAACC -3' (SEQ ID NO:5) or 5'-GCGCGGCTTACCCTTACCCTTAC-CCTAACC-3'(SEQ ID NO:6).

11. The method of claim 7 wherein the amplification products are detected via a labeled probe bound to the second primer.

12. The method of claim 11 wherein the label is selected from the group consisting of a radioactive molecule, a fluorescent molecule, a phosphorescent molecule, a ligand for a receptor, and an anchor group selected from biotin, avidin or streptavidin.

13. The method of claim 7 further comprising the step wherein the amplification products are immobilized on a solid phase via an anchor group.

14. The method of claim 13 wherein the anchor group is biotin and the solid phase is coated with avidin and/or streptavidin.

15. The method of claim 7 wherein the amplification product is labeled with an intercalating label selected from the group consisting of a radioactive molecule and a fluorescent molecule.

16. The method of claim 7 wherein the first primer lacks a telomeric repeat sequence.

17. The method of claim 16 wherein the first primer lacking a telomeric repeat sequence is 5'-AATCCGTCGAGCAGAGTT-3'(SEQ ID NO:3).

18. The method of claim 1, wherein the method is performed on a cell extract, the method further comprising normalizing the level of telomerase activity in the cell extract relative to the amount of RNA or protein in the cell extract.

19. A method for detecting a presence or an amount of telomerase activity, comprising:
  (a) binding an active telomerase ribonucleoprotein enzyme complex to a non-neutralizing antibody specific for the telomerase ribonucleoprotein enzyme complex bound to a solid support wherein the antibody is specific for the peptide sequence ARPAEEATSLEGALSGTRH (SEQ ID NO:2),
  (b) combining in a reaction vessel (1) telomerase ribonucleoprotein enzyme complex bound to the solid support from step (a), (2) a first primer, which is suitable as a telomerase substrate, and (3) a plurality of nucleoside triphosphates to form a reaction mixture, and incubating the reaction mixture under conditions to extend the first primer to produce an extension product; and
  (c) qualitatively or quantitatively detecting the extension product and correlating the detection with the presence or amount of telomerase activity.

20. A method for evaluating the biological response of a mammalian biological system exposed to a telomerase modulator comprising:
  (a) combining in a reaction vessel (1) an active telomerase ribonucleoprotein enzyme complex from the biological system bound to a solid support by a non-neutralizing anti-telomerase antibody that is specific for the peptide sequence ARPAEEATSLEGALSGTRH (SEQ ID NO:2),
  (2) a first primer, which is suitable as a telomerase substrate, and (3) a plurality of nucleoside triphosphates to form a reaction mixture, and incubating the reaction mixture under conditions to extend the first primer to produce an extension product;
  (b) qualitatively or quantitatively detecting the extension product and correlating the amount of extension product with the amount of telomerase activity; and
  (c) comparing the level of telomerase activity after administration of the modulator to the standard telomerase activity to determine the biological response of the subject.

21. The method of claim 20 wherein the mammalian biological system is a cell or tissue extract.

22. The method of claim 21 wherein the cell is a cancer cell, a skin cell, a hair follicle or a blood cell.

* * * * *

SEQUENCE LISTING

<160> NUMBER OF SEQ ID NOS: 7

<210> SEQ ID NO 1
<211> LENGTH: 1132
<212> TYPE: PRT
<213> ORGANISM: Homo sapiens

<400> SEQUENCE: 1

```
Met Pro Arg Ala Pro Arg Cys Arg Ala Val Arg Ser Leu Leu Arg Ser
1               5                   10                  15

Arg His Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60
```

```
Pro Pro Ala Ala Pro Ser Phe Arg Gln Val Ser Cys Leu Lys Glu Leu
 65                  70                  75                  80
Val Ala Arg Val Leu Gln Arg Leu Cys Glu Arg Gly Ala Lys Asn Val
                 85                  90                  95
Leu Ala Phe Gly Phe Ala Leu Leu Asp Gly Ala Arg Gly Gly Pro Pro
            100                 105                 110
Glu Ala Phe Thr Thr Ser Val Arg Ser Tyr Leu Pro Asn Thr Val Thr
        115                 120                 125
Asp Ala Leu Arg Gly Ser Gly Ala Trp Gly Leu Leu Leu Arg Arg Val
    130                 135                 140
Gly Asp Asp Val Leu Val His Leu Leu Ala Arg Cys Ala Leu Phe Val
145                 150                 155                 160
Leu Val Ala Pro Ser Cys Ala Tyr Gln Val Cys Gly Pro Pro Leu Tyr
                165                 170                 175
Gln Leu Gly Ala Ala Thr Gln Ala Arg Pro Pro His Ala Ser Gly
            180                 185                 190
Pro Arg Arg Arg Leu Gly Cys Glu Arg Ala Trp Asn His Ser Val Arg
            195                 200                 205
Glu Ala Gly Val Pro Leu Gly Leu Pro Ala Pro Gly Ala Arg Arg Arg
    210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
                245                 250                 255
Ala His Pro Gly Arg Thr Arg Gly Pro Ser Asp Arg Gly Phe Cys Val
            260                 265                 270
Val Ser Pro Ala Arg Pro Ala Glu Glu Ala Thr Ser Leu Glu Gly Ala
            275                 280                 285
Leu Ser Gly Thr Arg His Ser His Pro Ser Val Gly Arg Gln His His
    290                 295                 300
Ala Gly Pro Pro Ser Thr Ser Arg Pro Pro Arg Pro Trp Asp Thr Pro
305                 310                 315                 320
Cys Pro Pro Val Tyr Ala Glu Thr Lys His Phe Leu Tyr Ser Ser Gly
                325                 330                 335
Asp Lys Glu Gln Leu Arg Pro Ser Phe Leu Leu Ser Ser Leu Arg Pro
            340                 345                 350
Ser Leu Thr Gly Ala Arg Arg Leu Val Glu Thr Ile Phe Leu Gly Ser
        355                 360                 365
Arg Pro Trp Met Pro Gly Thr Pro Arg Arg Leu Pro Arg Leu Pro Gln
    370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
            420                 425                 430
Gly Ser Val Ala Ala Pro Glu Glu Glu Asp Thr Asp Pro Arg Arg Leu
        435                 440                 445
Val Gln Leu Leu Arg Gln His Ser Ser Pro Trp Gln Val Tyr Gly Phe
    450                 455                 460
Val Arg Ala Cys Leu Arg Arg Leu Val Pro Pro Gly Leu Trp Gly Ser
465                 470                 475                 480
```

```
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
            500                 505                 510
Ser Val Arg Asp Cys Ala Trp Leu Arg Arg Ser Pro Gly Val Gly Cys
        515                 520                 525
Val Pro Ala Ala Glu His Arg Leu Arg Glu Ile Leu Ala Lys Phe
    530                 535                 540
Leu His Trp Leu Met Ser Val Tyr Val Val Glu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
        595                 600                 605
His Arg Glu Ala Arg Pro Ala Leu Leu Thr Ser Arg Leu Arg Phe Ile
    610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro Pro
    690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
        755                 760                 765
Leu Gln Pro Tyr Met Arg Gln Phe Val Ala His Leu Gln Glu Thr Ser
    770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
        835                 840                 845
Met Glu Asn Lys Leu Phe Ala Gly Ile Arg Arg Asp Gly Leu Leu Leu
    850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
```

-continued

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 2
<211> LENGTH: 19
<212> TYPE: PRT
<213> ORGANISM: Homo sapiens

<400> SEQUENCE: 2

Ala Arg Pro Ala Glu Glu Ala Thr Ser Leu Glu Gly Ala Leu Ser Gly
1               5                   10                  15

Thr Arg His

<210> SEQ ID NO 3
<211> LENGTH: 18
<212> TYPE: DNA
<213> ORGANISM: Artificial Sequence
<220> FEATURE:
<223> OTHER INFORMATION: telomerase substrate

<400> SEQUENCE: 3
aatccgtcga gcagagtt                                              18

<210> SEQ ID NO 4
<211> LENGTH: 24
<212> TYPE: DNA
<213> ORGANISM: Artificial Sequence

```
<220> FEATURE:
<223> OTHER INFORMATION: telomerase substrate

<400> SEQUENCE: 4
cccttaccct tacccttacc ctaa                                          24

<210> SEQ ID NO 5
<211> LENGTH: 24
<212> TYPE: DNA
<213> ORGANISM: Artificial Sequence
<220> FEATURE:
<223> OTHER INFORMATION: telomerase substrate

<400> SEQUENCE: 5
gcgcggctaa ccctaaccct aacc                                          24

<210> SEQ ID NO 6
<211> LENGTH: 30
<212> TYPE: DNA
<213> ORGANISM: Artificial Sequence
<220> FEATURE:
<223> OTHER INFORMATION: telomerase substrate

<400> SEQUENCE: 6
gcgcggctta cccttaccct taccctaacc                                    30

<210> SEQ ID NO 7
<211> LENGTH: 20
<212> TYPE: PRT
<213> ORGANISM: Homo sapiens

<400> SEQUENCE: 7

Cys Ala Arg Pro Ala Glu Glu Ala Thr Ser Leu Glu Gly Ala Leu Ser
 1               5                  10                  15

Gly Thr Arg His
            20
```